United States Patent [19]
Giele

[11] Patent Number: 5,176,136
[45] Date of Patent: Jan. 5, 1993

[54] PACEMAKER WITH IMPROVED CONNECTOR BLOCK

[75] Inventor: Vincent Giele, Dieren, Netherlands

[73] Assignee: Vitatron Medical, B.V., Dieren, Netherlands

[21] Appl. No.: 741,145

[22] Filed: Aug. 7, 1991

[51] Int. Cl.$^5$ .............................................. A61N 1/375
[52] U.S. Cl. .................................................. 128/419 P
[58] Field of Search ..................................... 128/419 P

[56] References Cited

U.S. PATENT DOCUMENTS

| | | | |
|---|---|---|---|
| Re. 31,990 | 9/1985 | Sluetz et al. | 128/419 P |
| 4,072,154 | 2/1978 | Anderson et al. | 128/419 P |
| 4,112,953 | 9/1978 | Shanker et al. | 128/419 P |
| 4,180,078 | 12/1979 | Anderson | 128/419 PG |
| 4,262,673 | 4/1981 | Kinney et al. | 128/419 P |
| 4,860,750 | 8/1989 | Frey et al. | 128/419 P |

FOREIGN PATENT DOCUMENTS 0052879  6/1982  European Pat. Off. .

*Primary Examiner*—William E. Kamm
*Assistant Examiner*—Scott M. Getzow
*Attorney, Agent, or Firm*—Woodcock Washburn Kurtz Mackiewicz & Norris

[57] ABSTRACT

A dual chamber pacemaker is provided having a connector of reduced width, enabling an overall thinner pacemaker case. The connector receives dual chamber leads and each pair of connector blocks corresponding to a respective one of the leads is tilted toward the center of the connector by a predetermined angle, e.g. about 6°. The tilt angle enables a thinner connector, and thus a thinner pacemaker case, while providing distinguishable axis points at the top of the connector.

12 Claims, 2 Drawing Sheets

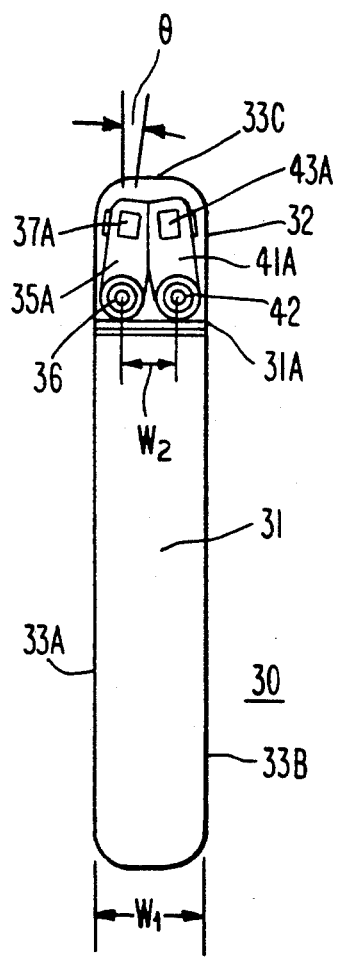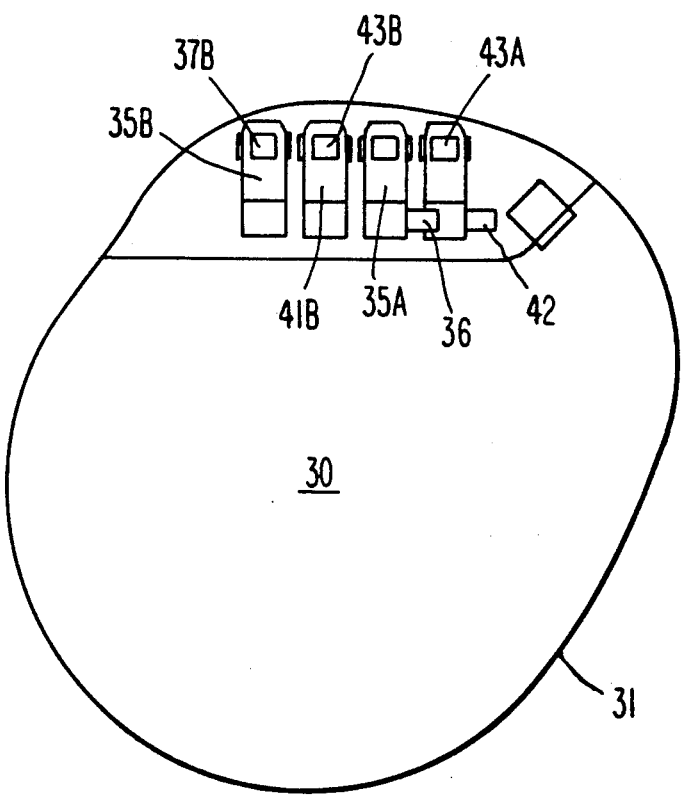
Fig. 1
Fig. 2

PACEMAKER WITH IMPROVED CONNECTOR BLOCK

FIELD OF THE INVENTION

This invention relates to implantable pacemaker devices and, more particularly, the connector portion of a dual chamber pacemaker which connects standard pacing leads to the pacemaker.

BACKGROUND OF THE INVENTION

It has long been recognized in the pacemaker field that the connector presents a limitation on reducing the size of an implantable pacemaker device. The connector performs the important function of providing mechanical and electrical connection between the pulse generator and other circuitry of the pacemaker, and the lead or leads which carry signals in each direction between the implanted pacemaker device and the patient's heart. Improved miniaturization of pacemaker circuitry has permitted a great reduction in the size of implantable pacemaker units, including a reduction of the thickness (width) of the units.

However, for certain reasons known in the art, the size of connector portion where the proximal end of the leads are connected to the pacemaker device cannot be arbitrarily reduced without sacrificing stress concentration on the leads and/or integrity of the connection.

In a typical prior art connector for a bipolar lead, the two lead pins are received in side-by-side jacks, an arrangement that imposes a limit on reducing the connector thickness. However, thickness can be reduced by replacing the side-by-side relation with what is referred to as an "over/under" arrangement for receiving the branches, or furculae of the lead. See, for example, U.S. Pat. No. 4,180,078, to Anderson. However, for dual chamber pacemakers requiring two leads for carrying signals to and from two chambers of the heart, there is generally employed a pair of in-line connector jacks, each jack receiving a bipolar lead which has a pair of conductor areas which are connected to terminal blocks. European Patent Application 0 052 879 illustrates a bipolar in-line connector for receiving an implantable lead. Generally, in such dual chamber arrangements, each of the two conductors of a bipolar in-line lead is connected to a respective terminal block and fixed to such block by a set screw which clamps the lead pin or surface area to the terminal block. The set screws are positioned in puncture plugs which must be large enough to accommodate them, and in practice the size of the puncture plugs has heretofore placed a lower limit on the width of the connector. A typical arrangement is that the set screws are accessed through the top of the connector block, typically by first fixing the pair of connections corresponding to one of the leads, and then fixing the pair corresponding to the other lead. The two jacks are generally side-by-side and separated across the width of the connector, with the connector blocks aligned upward so as to provide the access openings at the top of the device. Thus, viewing the connector from the top, there are two pairs of in-line openings through the top of the epoxy for accessing the set screws of the terminal blocks. The jacks can be positioned one on top of the other, but then the access openings are on the sides, which is less desirable ergonomically.

It is recognized that the potential advantage of further reduction in the width of a pacemaker is contingent upon also reducing the width of the connector, which should be flush with the sides of the pacemaker can or casing. In view of the above-noted limitations on reducing the size of the connector block, there remains a great need in the art for a connector block design which enables a reduced overall pacemaker size.

SUMMARY OF THE INVENTION

There is provided a pacemaker having a connector for receiving dual chamber leads, i.e., either bipolar or unipolar leads for electrically coupling the pacemaker to the patient's atrium and ventricle respectively. Each of the connector blocks for a first of the two leads, or channels, is tilted toward the center of the connector by about 6°, such that each atrial channel connector block is tilted from one side of the connector toward the center, and each ventricular channel connector block is tilted from the other side of the connector toward the center. The tilting enables a thinner connector, and thus a thinner pacemaker case, while providing distinguishable access points at the top of the connector. The tilt design enables the physician to push each channel lead in separately and fix the corresponding pair of set screws which are at the same tilt, without confusion.

BRIEF DESCRIPTION OF THE DRAWINGS

FIG. 1 is an end view of a pacemaker with the improved connector of this invention.

FIG. 2 is a side view of a pacemaker with the improved connector of this invention.

DESCRIPTION OF THE PREFERRED EMBODIMENTS

Figure 3:
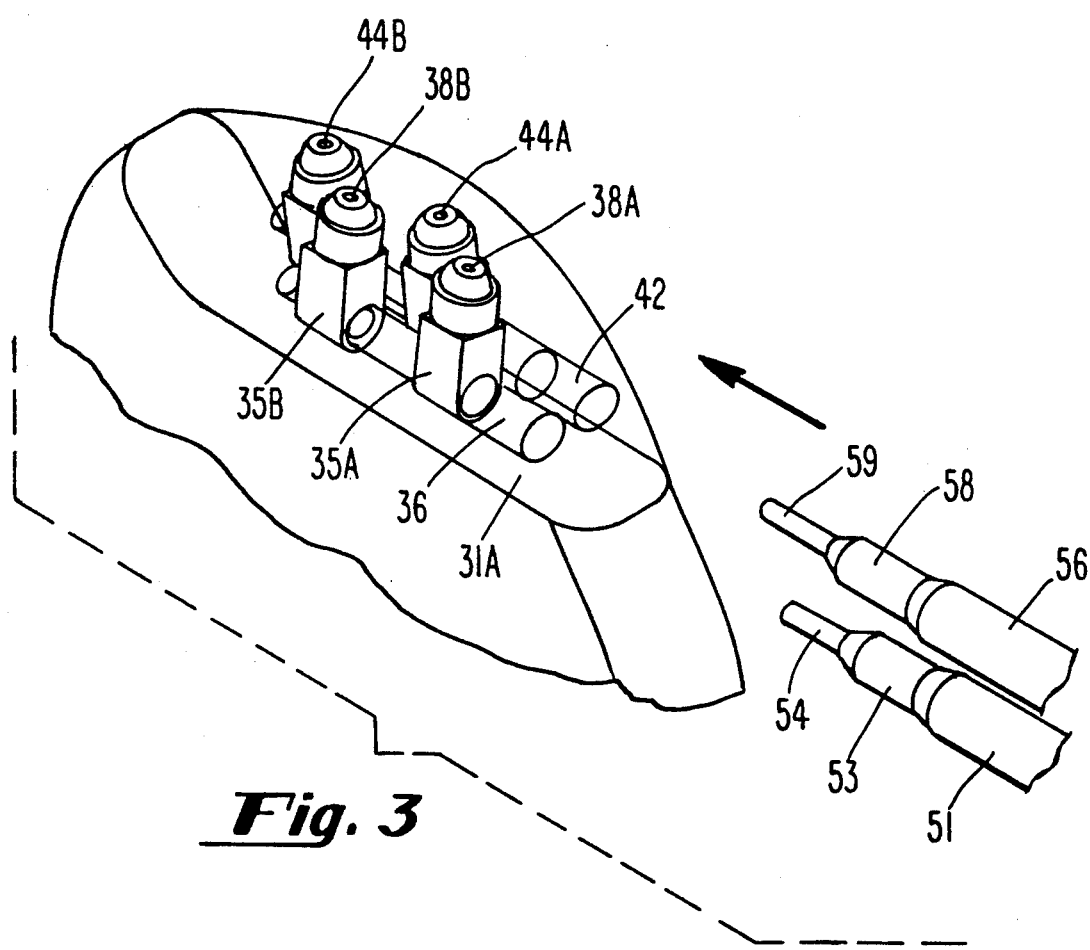
FIG. 3 is a perspective view showing the improved connector in accordance with this invention, and illustrating the relationship with a pair of leads.

Referring now to FIGS. 1, 2 and 3, there is shown a pacemaker 30 having a main casing 31 and a header block or connector 32. Casing 31 has a top edge 31A, to which the connector 32 is attached. The pacemaker 30 typically includes a pulse generator unit for generating stimulus pulses for delivery, e.g., for delivery to both the atrium and the ventricle in the case of a dual chamber device. The pacemaker also includes conventional circuitry for processing signals received from the heart and for making logic decisions, storing diagnostic data, timing out pulses, etc. Although in a preferred embodiment of this invention bipolar leads are illustrated for both chambers, unipolar pacing and/or sensing can be employed, in which case an indifferent electrode (not shown) is incorporated into the case 31 of the pacemaker unit.

As illustrated in FIG. 1, the sides of the casing 31 are flush with the connector 32. The connector portion is typically encased in epoxy, which defines sides 33A, 33B and top surface 33C. Utilizing the tilted connector block invention of this application, a pacemaker with a thickness $W_1$ of 8.5 mm has been achieved for side-to-side lead jacks. This is achieved with an epoxy coating minimum thickness of 0.5 mm.

As illustrated in the drawings, jacks 36, 42 are positioned side to side and run in parallel with side walls 33A, 33B. Jack 36 interconnects with connector blocks 35A, 35B, and jack 42 interconnects with blocks 41A, 41B. As is also conventional in the pacing art, each connector block has a terminal, or terminal block (not shown) where an exposed conductor area is connected to the terminal block, and secured by a set screw. Thus, by way of example, referring specifically to FIG. 3, the proximal end of atrial lead 51 is inserted into jack 36; conductor area 53 makes electrical contact with the terminal block of connector block 35A, and conductor area 54 makes electrical contact with the terminal block of connector block 35B. Next, the proximal end of lead 56 is inserted into jack 42; conductor area 58 makes electrical contact with the terminal block of connector block 41A, and conductor area 59 makes electrical contact with the terminal block of connector block 41B. Conductors, not shown, pass through the top edge 31A of the casing into the pacemaker to provide electrical communication between the pacemaker generator portion and the connector. Each lead, of course, provides electrical conduction between a terminal block and a respective electrode positioned in the heart. The conductor blocks 35A, 35B, 41A and 41B are suitable of conventional design, except for the tilt feature. In addition to a terminal block, each connector block comprises a puncture plug (37A, 37B, 43A, 43B). A depression in the epoxy above each puncture plug communicates down into the puncture plug, permitting access by a screw driver to a set screw (not shown), for clamping the lead. Also, a stop ring (not shown) is conventionally employed below each puncture plug to prevent the possibility that the set screw is rotated out of the junction block. Each connector block thus includes a terminal block, a puncture plug, and an access port by which the physician accesses the set screw to clamp the lead to the terminal block all in a known manner. As is seen particularly from the perspective view of FIG. 3, where the epoxy is not illustrated, the pair of access openings 38A, B for a first of the channel leads is positioned on one side of the top of the pacemaker, while the access openings 44A, B for the other channel lead are positioned on the other side.

In the pacemaker system of this invention, each connector block is tilted about a pivot point substantially coincident with the axis of its jack, 36 or 42. That is, each connector block, in its extension from the bottom to the top as illustrated, tilts in toward the center of the connector top 33C. As is seen in FIG. 1, the distance between the center lines of jacks 36 and 42 is illustrated as $W_2$, and in the preferred embodiment this distance is 4.1 mm. If there were no inward tilt to the connector blocks, the puncture plugs would cause a lateral extension of the epoxy around them. By tilting the connector blocks inward at about 6° ($\Theta$, as seen in FIG. 1), there remains sufficient space around the puncture plugs in order to provide the minimum 0.5 mm of epoxy, and still have a smooth continuous side surface which is flush with the casing, as illustrated in FIG. 1. Further, a tilt of about 6°, ±1°, not only enables the smaller width, but it enables a reduced height to the top of the connector block. Additionally, this tilt leaves each pair of connector block access openings at the top sufficiently displaced from each other that the physician has no trouble distinguishing which openings go with which lead. It is seen that if the tilt were increased beyond about 6° ±1°, the openings would tend to come in line with each other, which causes confusion. With this arrangement, the physician can put a first lead into one of the jacks, i.e., jack 36, and adjust the two set screws that communicate with the terminal blocks that connect with that jack; and then insert the proximal end of the other lead and adjust the other two set screws.

It is to be noted that while a tilt of about 6° is preferred, for the reasons above stated, the size reduction can be achieved by greater tilts. Thus, even if the top access openings were brought roughly in line by a greater tilt, connector size reduction would still be obtained. Further, each connector block could be rotated past the centerline of the top 33C, i.e., so that the access openings that communicate with each jack are positioned substantially above the other jack. While this arrangement is not preferred, due to the possibility of confusion, it would achieve connector size reduction and is within the scope of the invention. Thus, as utilized in this invention, tilt of the connector block means tilting each connector block away from its adjacent sidewall toward the opposite sidewall. Alternately, tilt is defined as the angle by which a connector block is rotated toward the connector blocks of the other jack, or toward the other jack. The tilt is preferably of a sufficient angle so that the outer wall of the connector can be formed with a minimum of about 0.5 mm epoxy at any point on the connector surface. Thus, for a distance $W_2$ of 4.1 mm between the jack centerlines, a tilt of at least about 5° permits a connector with sidewalls of no greater than 8.5 mm at any point.

It is to be noted that the axial, or longitudinal spacing of the connector blocks is in accordance with conventional pacemaker standards. Thus, the spacing between first and second contact portions of each bipolar lead (53, 54, 58, 59) is a standard 9.5 mm, such that the centerlines of the connector blocks for each channel are also spaced apart 9.5 mm. The design thus involves no change in the jacks which receive the proximal ends of the leads.

While the preferred embodiment has been illustrated showing the terminal blocks extending up to the top 33C of the connector surface, the terminal blocks can likewise be positioned so that they are each angled about 90° from the arrangement shown in FIGS. 1-3. Thus, the jack openings would be positioned over-/under, instead of side-by-side, and each connector block would extend from one side toward the other, with the blocks of the first channel being tilted toward the top of the connector outer surface, and the blocks of the second channel being tilted toward the bottom of the connector, providing side access through the epoxy to the puncture plugs instead of top access. Although such a side-access arrangement is not user preferred, it is within the scope of the invention, and may be functionally equivalent in terms of reducing connector size.

What is claimed:

1. A pacemaker having a connector portion adapted for connecting a pair of leads to said pacemaker, said pacemaker connector having first and second jacks, each jack presenting an opening for receiving one of said leads, at least one connector block associated with each said jack, and each of said connector blocks being tilted by at least about 6° toward the other jack.

2. The pacemaker as described in claim 1, wherein said pacemaker is a dual chamber pacemaker and has a pulse generator portion housed in a casing with sidewalls, and said connector has an outer surface with sidewalls, said casing sidewalls and said connector sidewalls being substantially flush with each other, the pacemaker thereby having a substantially uniform thickness.

3. The pacemaker as described in claim 2, wherein said connector comprises epoxy forming said outer surface, said epoxy having a minimum thickness of 0.5 mm, and further wherein said thickness is no greater than 8.5 mm.

4. The pacemaker as described in claim 2, wherein each of said connector blocks is adjacent to one of said connector sidewalls, and tilts away from said adjacent sidewall.

5. The pacemaker as described in claim 1, wherein each said jack has two connector blocks, and the two connector blocks of each jack tilt about 6° toward the connector blocks of the other jack.

6. The pacemaker as described in claim 2, wherein said connector outer surface has a top surface between said connector sidewalls, said top surface having access holes for accessing said connector blocks.

7. The pacemaker as described in claim 6, wherein said jacks are positioned side-by-side and run substantially parallel with said connector sidewalls, each said jack being adjacent to a respective one of said sidewalls, each of said connector blocks tilting away from said sidewall toward the center of the connector at an angle of about 6°.

8. The pacemaker as described in claim 7, wherein said connector has a width between said sidewalls no greater than 8.5 mm.

9. The pacemaker as described in claim 8, wherein said jacks have center axes spaced apart about 4.1 mm.

10. The pacemaker as described in claim 9, in combination with two bipolar leads, each lead having a pair of separate contact areas at its proximal end, said jack having terminal means for electrically coupling to each of said contact areas.

11. A pacemaker system comprising a pacemaker and a pair of leads, each of said leads carrying two conductors and having in-line conductor areas at its proximal end, said pacemaker having a connector portion and side-by-side axial jacks extending substantially in parallel in said connector portion, said connector portion also having a pair of tilted connector blocks each associated with a respective one of said jacks, each connector block having means for electrically coupling with one of said in-line conductor areas, the connector blocks coupled to each jack being tilted about the axis of the associated jack toward the connector blocks coupled to the other jack.

12. A pacemaker having a casing with first and second sidewalls of predetermined dimensions and a top edge, said casing further having a thickness between said sidewalls which is small compared to said dimensions;

said pacemaker having a connector portion connected to said casing top edge and having an outer surface including connector side surfaces substantially parallel to and flush with said casing side walls, said connector portion having a thickness between said connector sidewalls which is substantially the same as the thickness between said casing sidewalls;

said connector portion having an epoxy coating which forms said outer surface;

first and second side-by-side jacks in said connector, each said jack being adjacent to a respective side surface;

first and second connector block means for connecting to a respective contact area of a first lead to be positioned in said first jack;

third and fourth connector block means for connecting to respective contact areas of a second lead to be positioned in said second jack; and each connector block defining an axis between its jack and said connector top surface, said axis being tilted away from the connector side to which it is adjacent.

* * * * *